United States Patent [19]

Hay et al.

[11] Patent Number: 4,895,591
[45] Date of Patent: Jan. 23, 1990

[54] HERBICIDAL SULFONAMIDES

[75] Inventors: James V. Hay, Newark; Barry A. Wexler, Wilmington, both of Del.; Donna F. Zimmerman, Landenberg, Pa.

[73] Assignee: E. I. Du Pont de Nemours and Company, Wilmington, Del.

[21] Appl. No.: 238,102

[22] Filed: Aug. 30, 1988

Related U.S. Application Data

[60] Division of Ser. No. 111,670, Oct. 23, 1987, Pat. No. 4,786,313, Division of Ser. No. 917,930, Oct. 10, 1986, Pat. No. 4,721,521, Division of Ser. No. 768,158, Aug. 26, 1985, abandoned, Continuation-in-part of Ser. No. 680,549, Dec. 11, 1984, abandoned.

[51] Int. Cl.$^4$ .................. C07D 251/20; A01N 43/66
[52] U.S. Cl. ....................................... 71/93; 544/219; 544/113
[58] Field of Search ..................... 71/93; 544/219, 113

[56] References Cited

U.S. PATENT DOCUMENTS

| 4,368,069 | 1/1983 | Chen et al. | 71/93 |
| 4,435,206 | 3/1984 | Levitt | 71/92 |
| 4,579,583 | 4/1986 | Föry et al. | 71/92 |
| 4,784,684 | 11/1988 | Rorer | 71/93 |
| 4,806,142 | 2/1989 | Shapiro | 71/92 |

FOREIGN PATENT DOCUMENTS

| 30142 | 6/1981 | European Pat. Off. |
| 59-152684 | 2/1986 | Japan |
| 83/3779 | 11/1983 | South Africa |
| 836449 | 1/1984 | South Africa |
| 84/2722 | 10/1984 | South Africa |
| 84/6610 | 2/1985 | South Africa |

Primary Examiner—John M. Ford

[57] ABSTRACT

The invention relates to certain pyridine sulfonamide compounds having haloalkenyl substituents ortho to the sulfonylurea linkage.

21 Claims, No Drawings

HERBICIDAL SULFONAMIDES

This is a division of application Ser. No. 111,670, filed October 23, 1987, now U.S. Pat. No. 4,786,313, which is a division of application Ser. No. 917,930, filed October 10, 1986, now U.S. Pat. No. 4,721,521, which is a division of application Ser. No. 768,158, filed August 26, 1985, now abandoned, which is a continuation-in-part of application Ser. No. 680,549, filed December 11, 1984, now abandoned.

BACKGROUND OF THE INVENTION

The invention relates to certain pyridine sulfonamide compounds having haloalkenyl, substituents ortho to the sulfonylurea linkage, agriculturally suitable compositions thereof and method of their use as herbicides or plant growth regulants.

In the most common situation, the control of undesired vegetation is desired to permit the growth of useful crops such as cotton, rice, corn, wheat and soybeans, to name a few. Unchecked weed growth in such useful crops can cause significant losses, reducing profit to the farmer and increasing costs to the consumer. In other situations, herbicides are desired which will control all plant growth. Examples of areas in which complete control of all vegetation is desired are areas around fuel storage tanks, ammunition depots and industrial storage areas. There are many products commercially available for these purposes, but the search continues for products which are more effective, less costly and environmentally safe.

U.S. Pat. No. 4,368,069 discloses herbicidal benzenesulfonamides of formula

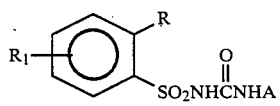

wherein

R is $-(CR_5R_6)_n-R_2$;
n is 0 or 1; and
$R_2$ may be $C_5-C_6$ cycloalkenyl or $C_2-C_5$ alkenyl.

South African patent application No. 83/3779 discloses herbicidal sulfonamides of formula

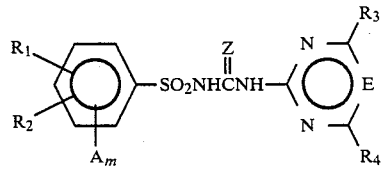

wherein

A is a radical of the formula C≡CR; and
R is, among others, a variety of alkyl or substituted alkyl groups.

Herbicidal thiophene sulfonamides are disclosed in European patent application (EP-A) No. 30,142, published June 10, 1981.

Herbicidal pyridinesulfonamides are disclosed in European patent application (EP-A) No. 13,480, published July 23, 1980.

U.S. Pat. No. 4,420,325 discloses herbicidal sulfonamides of the following formula

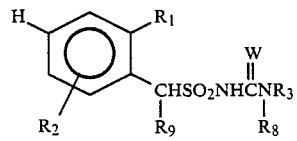

wherein $R_1$ is F, Cl, Br, $CF_3$, $C_1-C_3$ alkoxy, $C_1-C_3$ alkyl, $NO_2$, $CO_2R_4$, $SO_2R_5$, $SO_2NR_6R_7$, $SO_2N(OCH_3)CH_3$, $SO_2CH_2CF_3$, $OSO_2R_5$ or $CH_2L$; and
$R_9$ is H or $C_1-C_3$ alkyl.

South African patent application No. 84/2722, published 10/13/84, discloses herbicidal sulfonamides of formula

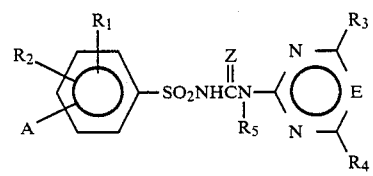

wherein

A is a radical of formula $-CR_6R_7XR_8$, $CR_9R_{10}R_{11}$ or $CHR_7SCQR_{21}$;
$R_6$ is H, $C_1-C_4$ alkyl or fluorine;
$R_7$ is H or $CH_3$;
X is O, S, SO or $SO_2$;
$R_8$ may be $C_2-C_5$ haloalkenyl, $C_3-C_5$ alkynyl, etc.

South African patent application No. 84/6610 discloses herbicidal pyrazolesulfonylureas of formula

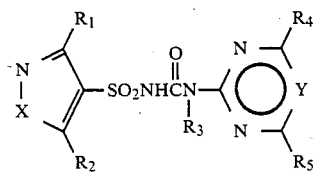

wherein

X is O or $NR_6$;
$R_1$ and $R_2$ are independently H, halogen, $C_1-C_6$ alkyl, $C_2-C_6$ alkenyl or $C_2-C_6$ alkynyl, which are optionally substituted by 1-3 halogen atoms, $C_1-C_4$ alkoxy, $C_1-C_4$ alkylsulfenyl, $C_1C_4$ alkylsulfinyl, $C_1-C_4$ alkylsulfonyl, OH, etc.

South African patent application No. 83/6449, published 3/1/84, discloses herbicidal sulfonylureas of the formula

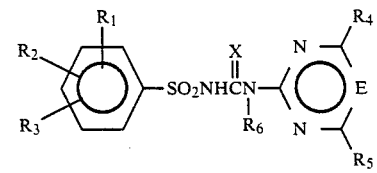

wherein $R_3$ is $C_2-C_{10}$ alkenyl which is substituted by, inter alia, one or more fluorine or bromine atoms or by one or more hydroxyl, cyano or nitro groups.

European Publication No. 132,230, published 1/23/85, discloses a process for preparing sulfonylureas of the formula

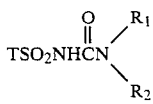

wherein

T denotes a substituted phenyl radical of formula

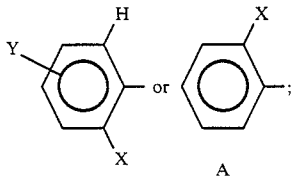

X is, inter alia, H, halogen, $C_2$-$C_4$ alkynyl;
$R_1$ is H or $C_1$-$C_4$ alkyl; and

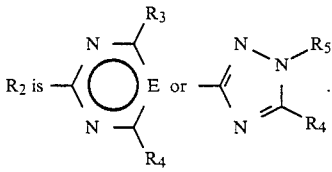

SUMMARY OF THE INVENTION

New compounds have been discovered which possess herbicidal activity as well as agriculturally suitable compositions thereof and a method of their use as general and/or selective preemergent and/or postemergent herbicides or plant growth regulators. Accordingly the compounds of the invention possessing herbicidal activity are compounds of the formula

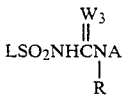    I wherein

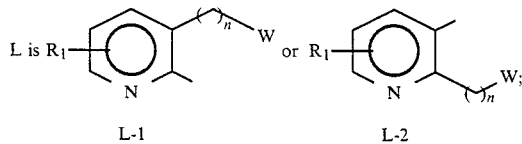

R is H or $CH_3$;
$W_3$ is O or S;
n is 0 or 1;
$R_1$ is H, $C_1$-$C_3$ alkyl, $C_1$-$C_3$ haloalkyl, halogen, nitro, $CH_2CN$, $CH_2OCH_3$, $CH_2SCH_3$, CN, $C_1$-$C_3$ alkoxy, $SO_2NR^IR^{II}$, $C_1$-$C_3$ alkylthio, $C_1$-$C_3$ alkylsulfinyl, $C_1$-$C_3$ alkylsulfonyl or $CO_2R^{III}$;
$R^I$ is H, $C_1$-$C_4$ alkyl, $C_2$-$C_3$ cyanoalkyl, methoxy or ethoxy;
$R^{II}$ is H, $C_1$-$C_4$ alkyl or $C_3$-$C_4$ alkenyl; or
$R^I$ and $R^{II}$ may be taken together as $-(CH_2)_3-$, $-(CH_2)_4-$, $-(CH_2)_5-$ or $-CH_2CH_2OCH_2CH_2-$;

$R^{III}$ is $C_1$-$C_4$ alkyl, $C_3$-$C_4$ alkenyl, $C_3$-$C_4$ alkynyl, $C_2$-$C_4$ haloalkyl, $C_2$-$C_4$ cyanoalkyl, $C_5$-$C_6$ cycloalkyl, $C_4$-$C_7$ cycloalkylalkyl or $C_2$-$C_4$ alkoxyalkyl;
W is $W_1$;
$W_1$ is $C_2$-$C_8$ alkenyl substituted with 1-3 atoms of F, Cl or Br:

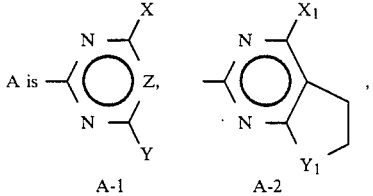

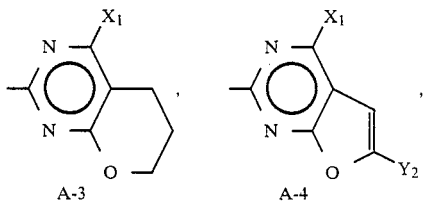

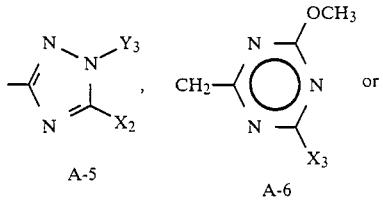

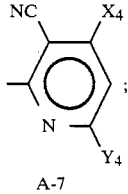

X is H, $C_1$-$C_4$ alkyl, $C_1$-$C_4$ alkoxy, $C_1$-$C_4$ haloalkoxy, $C_1$-$C_4$ haloalkyl, $C_1$-$C_4$ haloalkylthio, $C_1$-$C_4$ alkylthio, halogen, $C_2$-$C_5$ alkoxyalkyl, $C_2$-$C_5$ alkoxyalkoxy, amino, $C_1$-$C_3$ alkylamino or di($C_1$-$C_3$ alkyl)amino;
Y is H, $C_1$-$C_4$ alkyl, $C_1$-$C_4$ alkoxy, $C_1$-$C_4$ haloalkoxy, $C_1$-$C_4$ haloalkylthio, $C_1$-$C_4$ alkylthio, $C_2$-$C_5$ alkoxyalkyl, $C_2$-$C_5$ alkoxyalkoxy, amino, $C_1$-$C_3$ alkylamino, di($C_1$-$C_3$ alkyl)amino, $C_3$-$C_4$ alkenyloxy, $C_3$-$C_4$ alkynyloxy, $C_2$-$C_5$ alkylthioalkyl, $C_1$-$C_4$ haloalkyl, $C_3$-$C_5$ cycloalkyl,

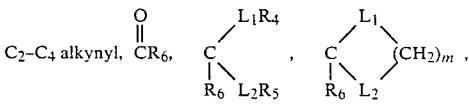

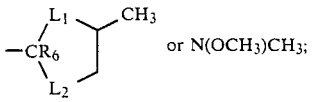

m is 2 or 3;
$L_1$ and $L_2$ are independently O or S;
$R_4$ and $R_5$ are independently $C_1$-$C_2$ alkyl;
$R_6$ is H or $CH_3$;
Z is CH or N;

$Y_1$ is O or $CH_2$;
$X_1$ is $CH_3$, $OCH_3$, $OC_2H_5$ or $OCF_2H$;
$Y_2$ is H or $CH_3$;
$X_2$ is $CH_3$, $OCH_3$ or $SCH_3$;
$Y_3$ is $CH_3$, $CH_2CH_3$ or $CH_2CF_3$;
$X_3$ is $CH_3$ or $OCH_3$;
$Y_4$ is $CH_3$, $OCH_3$, $OC_2H_5$ or Cl; and
$X_4$ is $CH_3$, $OCH_3$, $OC_2H_5$ or $CH_2OCH_3$;
and their agriculturally suitable salts; provided that (a) when X is Cl, F, Br or I, then Z is CH and Y is $OCH_3$, $OC_2H_5$, $N(OCH_3)CH_3$, $NHCH_3$, $N(CH_3)_2$ or $OCF_2H$;

(b) when X or Y is $OCF_2H$ then Z is CH;

(c) when $W_3$ is S, then R is H, A is A-1, and Y is $CH_3$, $OCH_3$, $OC_2H_5$, $CH_2OCH_3$, $C_2H_5$, $CF_3$, $SCH_3$, $OCH_2CH=CH_2$, $OCH_2C\equiv CH$, $OCH_2CH_2OCH_3$ or $CH(OCH_3)_2$; and (d) when the total number of carbon atoms of X and Y is greater than four, then the number of carbons of $R_1$ must be less than or equal to two and the number of carbons of W must be less than or equal to four.

In the above definitions, the term "alkyl" used either alone or in compound words such as "alkylthio" or "haloalkyl", denotes straight chain or branched alkyl, e.g., methyl, ethyl, n-propyl, isopropyl or the different butyl isomers.

Alkoxy denotes methoxy, ethoxy, n-propoxy, isopropoxy and the different butoxy isomers.

Alkenyl denotes straight chain or branched alkenes, e.g., vinyl, 1-propenyl, 2-propenyl, 3-propenyl and the different butenyl, pentenyl, hexenyl, heptenyl and octenyl isomers.

Alkynyl denotes straight chain or branched alkynes, e.g., ethynyl, 1-propynyl, 2-propynyl and the different butynyl, pentynyl, hexynyl, heptynyl and octynyl isomers.

Cyclohexenyl means cyclobutenyl, cyclopentenyl, cyclohexenyl and cycloheptenyl.

The term "halogen", either alone or in compound words such as "haloalkyl", denotes fluorine, chlorine, bromine or iodine.

In terms such as $C_2$-$C_3$ alkylthioalkyl, the specified number of carbon atoms is meant to define the total number of carbon atoms in that substituent group. For example, $C_2$-$C_3$ alkylthioalkyl would designate $CH_2SCH_3$, $CH_2SC_2H_5$, $CH_2CH_2SCH_3$ or $CH(CH_3)SCH_3$, and $C_2$-$C_5$ alkoxyalkoxy would represent $OCH_2OCH_3$ through $O(CH_2)_4OCH_3$ or $OCH_2O(CH_2)_3CH_3$ and the various structural isomers embraced therein.

Alkylsulfonyl denotes methylsulfonyl, ethylsulfonyl and the different propylsulfonyl isomers.

Alkylthio, alkylsulfinyl, alkylamino, alkylsulfamoyl, etc. are defined in an analogous manner.

The compounds of the invention which are preferred for reasons of increased ease of synthesis and/or greater herbicidal efficacy are:

(1) Compounds of Formula I where R is H; and $W_3$ is O.
(2) Compounds of Preferred 1 where $R_1$ is H, F, Cl, $NO_2$, $C_1$-$C_2$ alkyl, $C_1$-$C_2$ haloalkyl, $C_1$-$C_2$ alkoxy, $C_1$-$C_2$ alkylthio, $CH_2OCH_3$ or $CH_2SCH_3$, and is not para to the sulfonylurea bridge.
(3) Compounds of Preferred 2 where X is $CH_3$, $OCH_3$, $OC_2H_5$, Cl, F, Br, $OCF_2H$, $CH_2F$, $OCH_2CH_2F$, $OCH_2CHF_2$, $OCH_2CF_3$, $CF_3$, $CH_2Cl$ or $CH_2Br$; and Y is H, $C_1$-$C_3$ alkyl, $OCH_3$, $OC_2H_5$, $CH_2OCH_3$, $NHCH_3$, $N(OCH_3)CH_3$, $N(CH_3)_2$, $CF_3$, $SCH_3$, $OCH_2CH=CH_2$, $OCH_2C\equiv CH$, $CH_2OC_2H_5$, $OCH_2CH_2OCH_3$, $CH_2SCH_3$, $OCF_2H$, $SCF_2H$, cyclopropyl, $C\equiv CH$ or $C\equiv CCH_3$.
(4) Compounds of Preferred 3 where $W_1$ is $C_2$-$C_5$ alkenyl substituted by 1-3 atoms of F, Cl or Br;
(5) Compounds of Preferred 4 where A is A-1; X is $CH_3$, $OCH_3$, $OC_2H_5$, Cl or $OCF_2H$; Y is $CH_3$, $C_2H_5$, $OCH_3$, $CH_2OCH_3$, $CH(OCH_3)_2$, $OCF_2H$, $NHCH_3$, $N(CH_3)_2$ or cyclopropyl; and $R_1$ is H, $CH_3$, $OCH_3$ or Cl.
(6) Compounds of Preferred 4 where L is L-1.
(7) Compounds of Preferred 4 where L is L-2.

DETAILED DESCRIPTION OF THE INVENTION

Synthesis

The compounds of Formula I can be prepared by reacting an appropriate sulfonyl isocyanate or sulfonyl isothiocyanate, II, with an appropriately substituted aminoheterocycle, III, as shown in Equation 1, where R, $W_3$, A and L are as previously defined:

$$RNHA + LSO_2NCW \xrightarrow[24 \text{ hours}]{25-80° C.} I \qquad \text{Equation 1}$$
$$\text{III} \quad \text{II}$$

The reaction is best performed in an inert solvent such as methylene chloride or toluene at 25 to 100° C. for 1 to 24 hours. Isolation of the product can be achieved by concentrating the solution and trituration with an appropriate solvent such as butyl chloride.

Alternatively, compounds of Formula I, where $W_3$ is O, can be prepared by reacting the sulfonamides of Formula IV with the carbamates of Formula V ($R'=CH_3$) in the presence of an excess of trimethylaluminum, as shown in Equation 2, where L, R and A are as previously defined, provided $R_1$ is other than $CO_2R^{III}$.

$$LSO_2NH_2 + R'O\overset{O}{\overset{\|}{C}}-NRA \xrightarrow[CH_2Cl_2]{Me_3Al} I \qquad \text{Equation 2}$$
$$\text{IV} \qquad \text{V}$$

The reactions are best performed in an inert solvent such as methylene chloride at the reflux point of the solution (40° C.) for 10 to 24 hours. Isolation of the product is best achieved by exposing the reaction mixture to acetic acid, separation of the layers and concentrating the organic layer to a solid.

Alternatively, compounds of Formula I can be prepared by exposing a phenyl carbamate V ($R'=Ph$) to the sulfonamide IV in an appropriate solvent such as dioxane at 25° to 100° C. in the presence of a strong base such as 1,8-diazabicyclo[5.4.0]undec-7-ene; acid workup affords the desired product, as disclosed in European patent application (EP-A) No. 44,807. Compounds of Formula I can also be prepared from a phenyl carbamate V and the tert-butyldimethylsilane-protected sulfonamide IV ($LSO_2NHSi(CH_3)_2$-t-Bu). Addition of tetrabutylammonium fluoride to a mixture of the carbamate and sulfonamide affords, after workup, the desired product. The required carbamates can be prepared from the corresponding amines, III, and dimethyl- or diphenylcarbonate or methyl- or phenyl-chloroformate and a base such as sodium hydride.

The sulfonyl isocyanates, II, used in the preparation of I are known in the art and can be prepared by known methods. For examples, isocyanates can be prepared by exposing an appropriate benzene or heterocyclic sulfonamide to phosgene in the presence of an alkyl isocyanate and an amine catalyst such as 1,4-diazabicyclo[2.2.2]octane at the reflux point of the solvent. See H. Ulrich and A. A. Y. Sayigh, *Newer Methods of Preparative Organic Chemistry*, Vol. VI, p. 223–241, Academic Press, New York and London, W. Forest Ed.

Sulfonyl isothiocyanates of Formula II, where $W_3$ is S, can be prepared according to the method of K. Hartke, *Arch. Pharm.*, 299, 174 (1966).

The intermediate sulfonamides IV used to prepare the corresponding sulfonylureas I can be prepared in a variety of ways. For example, 1 may be prepared from 2 via the lithiation, condensation protocol outlined in Equation 3.

Equation 3

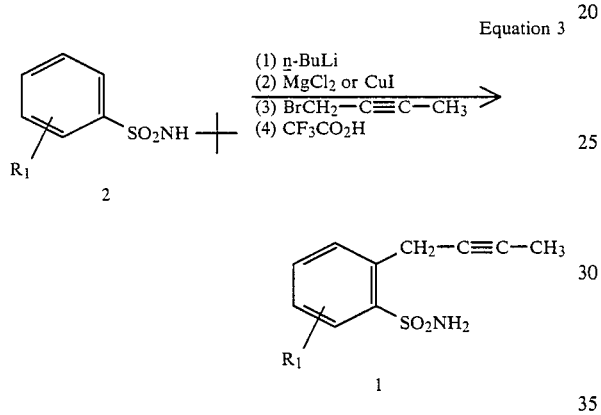

This same methodology can also be applied to other sulfonamides such as thiophene 3 and pyrazole 4 as outlined in Equation 4. The examples depicted are meant to be exemplary and the methodology is applicable to a wide range of values for W and the various aromatic thiophene, pyrazole, pyridine and benzyl isomers.

Equation 4

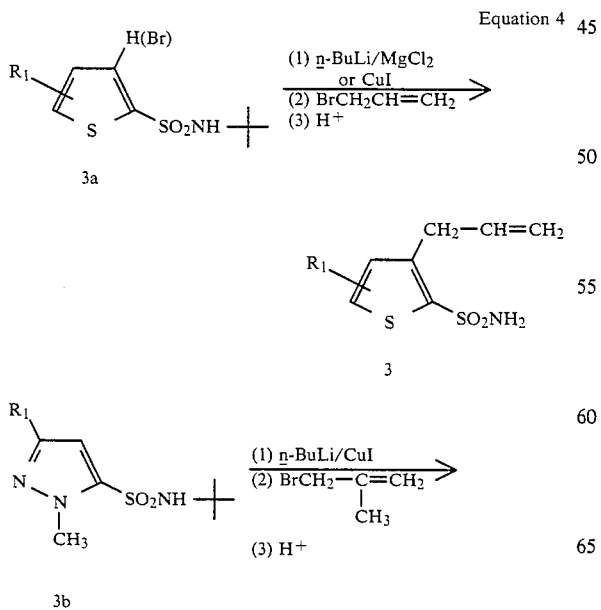

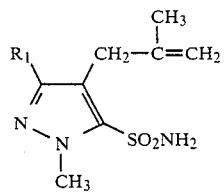

Sulfonamides such as 1, 3 and 4 can also be prepared from the corresponding olefin or alkyne as outlined in Equation 5, where W is as previously defined.

Equation 5

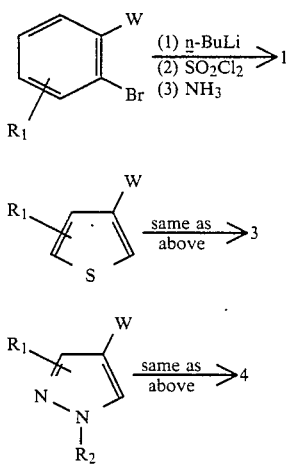

Olefinic sulfonamides such as 5 can be prepared from the methyl-substituted t-butylsulfonamide 6, as outlined in Equation 6. Here again, the example is intended to be exemplary and would be applicable to a wide variety of values for $R_1$ and $W_1$.

Equation 6

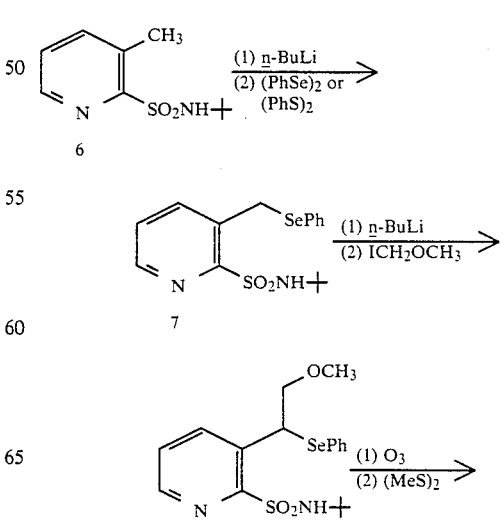

-continued
Equation 6

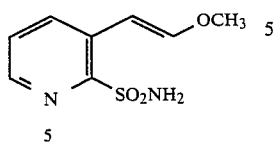

5

The sulfonamides IV of the invention such as 8 or 9 can also be prepared via a modification of the Ullman reaction as outlined in Equation 7.

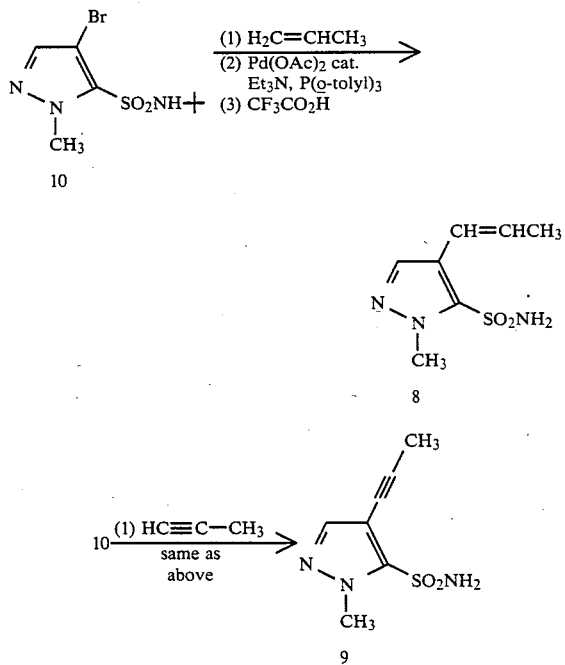

Intermediates such as 9 can also be used to prepare the corresponding olefins such as 8 via catalytic hydrogenation, employing a catalyst such as Lindlar catalyst.

Condensation of protected sulfonamides, for example 3c, with ketones and aldehydes followed by elimination also affords the desired sulfonamides. This is outlined in Equation 8.

Equation 8

Sulfonamides such as 3d can be prepared via the aldehyde 3e by a Knoevenagel type condensation with active methylene compounds as shown in Equation 9. Appropriate active methylene compounds include malonic esters, malononitrile, α-cyanoacetates, α-nitroacetates to name a few.

Equation 9

Similar condensation with pyrazole, pyridine or benzene aldehydes provides access to the corresponding difunctionalized alkenyl sulfonamides.

One skilled in the art will recognize that many of the methods described above can result in the formation of two possible geometrical isomers about the carbon-carbon double bond. This invention is meant to encompass all isomers. In cases where a mixture is obtained, the isomers can be separated by standard methods, such as fractional recrystallization or chromatography. Alternatively, the compounds can be used as a mixture of double bond isomers.

The intermediate pyrazole, thiophene, pyridine and benzyl sulfonamides are well known to one skilled in the art. For further information pertaining to their preparation see EP-A-95,925; EP-A-30,142; EP-A-13,480; EP-A-51,466; and U.S. Pat. No. 4,420,325. The lithiation of both aromatic and heterocyclic compounds is well known to one skilled in the art. For further information pertaining to this methodology see Stowell, J. C. "Carbanions in Organic Synthesis", John Wiley & Sons: New York, 1979; Snieckus, V. *Tetrahedron Lett.* 26, 1145 (1985) and ibid, 1149 (1985).

The heterocyclic amines of Formula III can be prepared by methods known in the literature or simple modifications thereof, by those skilled in the art. For instance, EP-A-84,224 (published July 27, 1983) and W. Braker et al, *J. Am. Chem. Soc.* 1947, 69, 3072 describe methods for preparing aminopyrimidines and triazines substituted by acetal groups. Also, South African patent application Nos. 825,045 and 825,671 describe methods for preparing aminopyrimidines and triazines substituted by haloalkyl or haloalkylthio groups such as $OCH_2CH_2F$, $OCH_2CF_3$, $SCF_2H$, and $OCF_2H$ among other groups. South African patent application No. 837,434 (published October 5, 1983) describes methods for the synthesis of cyclopropylpyrimidines and triazines substituted by such groups as alkyl, haloalkyl, alkoxy, haloalkoxy, alkylamino, dialkylamino, and alkoxyalkyl.

The 5,6-dihydrofuro[2.3-d]pyrimidin-2-amines, and the cyclopenta[d]pyrimidin-2-amines, of Formula III, where A is A-2, and the 6,7-dihydro-5H-pyrano-[2.3-d]pyrimidine-2-amines, of Formula III, where A is A-3, can be prepared as described in EP-A No. 15,863. The furo[2.3-d]pyrimidin-2-amines, of Formula III, where A is A-4, are described in EP-A No. 46,677. Heterocycles of formula III, where A is A-5, can be prepared as described in EP-A No. 73,562. Heterocycles of Formula III, where A is A-6, can be prepared by methods taught in EP-A-94,260. Compounds of Formula III, where A is A-7, can be prepared by methods taught in EP-A-125,864.

In addition, general methods for preparing aminopyrimidines and triazines have been reviewed in the following publications.

"The Chemistry of Heterocyclic Compounds", a series published by Interscience Publishers, Inc., New York and London;

"Pyrimidines", Vol. 16 of the same series by D. J. Brown;

"s-Triazines and Derivatives", Vol. 13 of the same series by E. M. Smolin and L. Rapaport; and F. C. Schaefer, U.S. Pat. No. 3,154,547 and K. R. Huffman and F. C. Schaefer, *J. Org. Chem.*, 28, 1812 (1963), which describe the synthesis of triazines.

Agriculturally suitable salts of compounds of Formula I are also useful herbicides and can be prepared in a number of ways known to the art. For example, metal salts can be made by contacting compounds of Formula I with a solution of an alkali or alkaline earth metal salt having a sufficiently basic anion (e.g., hydroxide, alkoxide or carbonate). Quaternary amine salts can be made by similar techniques.

Salts of compounds of Formula I can also be prepared by exchange of one cation for another. Cationic exchange can be effected by direct contacting of an aqueous solution of a salt of a compound of Formula I (e.g., alkali metal or quaternary amine salt) with a solution containing the cation to be exchanged. This method is most effective when the desired salt containing the exchanged cation is insoluble in water, e.g., a copper salt, and can be separated by filtration.

Exchange may also be effected by passing an aqueous solution of a salt of a compound of Formula I (e.g., an alkali metal or quaternary amine salt) through a column packed with a cation exchange resin containing the cation to be exchanged. In this method, the cation of the resin is exchanged for that of the original salt and the desired product is eluted from the column. This method is particularly useful when the desired salt is water-soluble, e.g., a potassium, sodium or calcium salt.

Acid addition salts, useful in this invention, can be obtained by reacting a compound of Formula I with a suitable acid, e.g., p-toluenesulfonic acid, trichloroacetic acid or the like.

Applying the methods described in Equations 1–8, one skilled in the art can prepare the compounds of Table I.

TABLE OF STRUCTURES

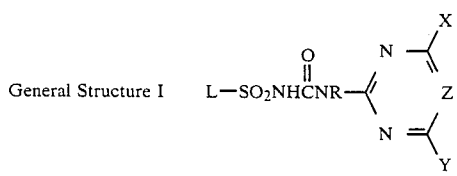

General Structure I   $L-SO_2NHCNR$

TABLE I

General Structure I

| L | n | W | R | $R_1$ | $R_2$ | X | Y | Z | m.p. (°C.) |
|---|---|---|---|---|---|---|---|---|---|
| L-1 | 0 | CH=CH—Br | H | H | — | $CH_3$ | $CH_3$ | CH | |
| L-1 | 0 | CH=CH—Br | H | H | — | $CH_3$ | $OCH_3$ | CH | |
| L-1 | 0 | CH=CH—Br | H | H | — | $OCH_3$ | $OCH_3$ | CH | |
| L-1 | 0 | CH=CH—Br | H | H | — | $CH_3$ | $CH_3$ | N | |
| L-1 | 0 | CH=CH—Br | H | H | — | $CH_3$ | $OCH_3$ | N | |
| L-1 | 0 | CH=CH—Br | H | H | — | $OCH_3$ | $OCH_3$ | N | |
| L-1 | 0 | CH=CH—Br | H | H | — | Cl | $OCH_3$ | CH | |
| L-1 | 0 | CH=CH—$CF_3$ | H | H | — | $CH_3$ | $CH_3$ | CH | |
| L-1 | 0 | CH=CH—$CF_3$ | H | H | — | $CH_3$ | $OCH_3$ | CH | |
| L-1 | 0 | CH=CH—$CF_3$ | H | H | — | $OCH_3$ | $OCH_3$ | CH | |
| L-1 | 0 | CH=CH—$CF_3$ | H | H | — | $CH_3$ | $CH_3$ | N | |
| L-1 | 0 | CH=CH—$CF_3$ | H | H | — | $CH_3$ | $OCH_3$ | N | |
| L-1 | 0 | CH=CH—$CF_3$ | H | H | — | $OCH_3$ | $OCH_3$ | N | |
| L-1 | 0 | CH=CH—$CF_3$ | H | H | — | Cl | $OCH_3$ | CH | |
| L-1 | 1 | BrC=$CH_2$ | H | H | — | $CH_3$ | $CH_3$ | CH | |
| L-1 | 1 | BrC=$CH_2$ | H | H | — | $CH_3$ | $OCH_3$ | CH | |
| L-1 | 1 | BrC=$CH_2$ | H | H | — | $OCH_3$ | $OCH_3$ | CH | |
| L-1 | 1 | BrC=$CH_2$ | H | H | — | $CH_3$ | $CH_3$ | N | |
| L-1 | 1 | BrC=$CH_2$ | H | H | — | $CH_3$ | $OCH_3$ | N | |
| L-1 | 1 | BrC=$CH_2$ | H | H | — | $OCH_3$ | $OCH_3$ | N | |
| L-1 | 1 | BrC=$CH_2$ | H | H | — | Cl | $OCH_3$ | CH | |
| L-1 | 1 | HC=CH$CH_2$Br | H | H | — | $CH_3$ | $CH_3$ | CH | |
| L-1 | 1 | HC=CH$CH_2$Br | H | H | — | $CH_3$ | $OCH_3$ | CH | |
| L-1 | 1 | HC=CH$CH_2$Br | H | H | — | $OCH_3$ | $OCH_3$ | CH | |
| L-1 | 1 | HC=CH$CH_2$Br | H | H | — | $CH_3$ | $CH_3$ | N | |
| L-1 | 1 | HC=CH$CH_2$Br | H | H | — | $CH_3$ | $OCH_3$ | N | |
| L-1 | 1 | HC=CH$CH_2$Br | H | H | — | $OCH_3$ | $OCH_3$ | N | |
| L-1 | 1 | HC=CH$CH_2$Br | H | H | — | Cl | $OCH_3$ | CH | |
| L-2 | 0 | CH=CH—Br | H | H | — | $CH_3$ | $CH_3$ | CH | |
| L-2 | 0 | CH=CH—Br | H | H | — | $CH_3$ | $OCH_3$ | CH | |
| L-2 | 0 | CH=CH—Br | H | H | — | $OCH_3$ | $OCH_3$ | CH | |
| L-2 | 0 | CH=CH—Br | H | H | — | $CH_3$ | $CH_3$ | N | |
| L-2 | 0 | CH=CH—Br | H | H | — | $CH_3$ | $OCH_3$ | N | |
| L-2 | 0 | CH=CH—Br | H | H | — | $OCH_3$ | $OCH_3$ | N | |
| L-2 | 0 | CH=CH—Br | H | H | — | Cl | $OCH_3$ | CH | |
| L-2 | 0 | CH=CH—$CF_3$ | H | H | — | $CH_3$ | $CH_3$ | CH | |
| L-2 | 0 | CH=CH—$CF_3$ | H | H | — | $CH_3$ | $OCH_3$ | CH | |
| L-2 | 0 | CH=CH—$CF_3$ | H | H | — | $OCH_3$ | $OCH_3$ | CH | |
| L-2 | 0 | CH=CH—$CF_3$ | H | H | — | $CH_3$ | $CH_3$ | N | |
| L-2 | 0 | CH=CH—$CF_3$ | H | H | — | $CH_3$ | $OCH_3$ | N | |
| L-2 | 0 | CH=CH—$CF_3$ | H | H | — | $OCH_3$ | $OCH_3$ | N | |
| L-2 | 0 | CH=CH—$CF_3$ | H | H | — | Cl | $OCH_3$ | CH | |
| L-2 | 1 | BrC=$CH_2$ | H | H | — | $CH_3$ | $CH_3$ | CH | |
| L-2 | 1 | BrC=$CH_2$ | H | H | — | $CH_3$ | $OCH_3$ | CH | |
| L-2 | 1 | BrC=$CH_2$ | H | H | — | $OCH_3$ | $OCH_3$ | CH | |
| L-2 | 1 | BrC=$CH_2$ | H | H | — | $CH_3$ | $CH_3$ | N | |
| L-2 | 1 | BrC=$CH_2$ | H | H | — | $CH_3$ | $OCH_3$ | N | |
| L-2 | 1 | BrC=$CH_2$ | H | H | — | $OCH_3$ | $OCH_3$ | N | |
| L-2 | 1 | BrC=$CH_2$ | H | H | — | Cl | $OCH_3$ | CH | |
| L-2 | 1 | HC=CH$CH_2$Br | H | H | — | $CH_3$ | $CH_3$ | CH | |
| L-2 | 1 | HC=CH$CH_2$Br | H | H | — | $CH_3$ | $OCH_3$ | CH | |
| L-2 | 1 | HC=CH$CH_2$Br | H | H | — | $OCH_3$ | $OCH_3$ | CH | |
| L-2 | 1 | HC=CH$CH_2$Br | H | H | — | $CH_3$ | $CH_3$ | N | |
| L-2 | 1 | HC=CH$CH_2$Br | H | H | — | $CH_3$ | $OCH_3$ | N | |
| L-2 | 1 | HC=CH$CH_2$Br | H | H | — | $OCH_3$ | $OCH_3$ | N | |
| L-2 | 1 | HC=CH$CH_2$Br | H | H | — | Cl | $OCH_3$ | CH | |

Formulations

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used at intermediates for further formulation. The formulations, broadly, contain about 0.1% to 99% by weight of active ingredient(s) and at least one of (a) about 0.1% to 20% surfactant(s) and (b) about 1% to 99.9% solid or liquid inert diluent(s). More specifically, they will contain these ingredients in the following approximate proportions:

|  | Active | Weight Percent* | |
|---|---|---|---|
|  | Ingredient | Diluent(s) | Surfactant(s) |
| Wettable Powders | 20–90 | 0–74 | 1–10 |
| Oil Suspensions, Emulsions, Solutions, (including Emulsifiable Concentrates) | 3–50 | 40–95 | 0–15 |
| Aqueous Suspension | 10–50 | 40–84 | 1–20 |
| Dusts | 1–25 | 70–99 | 0–5 |
| Granules and Pellets | 0.1–95 | 5–99.9 | 0–15 |
| High Strength Compositions | 90–99 | 0–10 | 0–2 |

* Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, New Jersey, but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates: solution concentrates are preferably stable against phase separation at 0° C. "McCutcheon's Detergents and Emulsifiers Annual", MC Publishing Corp., Ridgewood, New Jersey, as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", *Chemical Engineering*, December 4, 1967, pp. 147ff, and "Perry's Chemical Engineer's Handbook", 5th Ed., McGraw-Hill, New York, 1973, pp. 8-57ff.

For further information regarding the art of formulation, see for example:

H. M. Loux, U.S. Pat. No. 3,235,361, February 15, 1966, Col. 6, line 16 through Col. 7, line 19 and Examples 10 through 41;

R. W. Luckenbaugh, U.S. Pat. No. 3,309,192, March 14, 1967, Col. 5, line 43 through Col. 7, line 62 and Examples 8, 12, 15, 39, 41, 52, 53, 58, 132, 138–140, 162–164, 166, 167 and 169–182;

H. Gysin and E. Knusli, U.S. Pat. No. 2,891,855, June 23, 1959, Col. 3, line 66 through Col. 5, line 17 and Examples 1–4;

G. C. Klingman, "Weed Control as a Science", John Wiley and Sons, Inc., New York, 1961, pp. 81–96; and J. D. Fryer and S. A. Evans, "Weed Control Handbook", 5th Ed., Blackwell Scientific Publications, Oxford, 1968, pp. 101–103.

In the following examples, all parts are by weight unless otherwise indicated.

EXAMPLE 1

Wettable Power

3-[1-(1,2-difluoro-2-chloroethenyl)]-N-[4-methoxy-6-methylpyrimidin-2-yl)aminocarbonyl]-2-pyridine-sulfonamide 80% sodium alkylnaphthalenesulfonate 2%
sodium ligninsulfonate 2%
synthetic amorphous silica 3%
kaolinite 13%

The ingredients are blended, hammer-milled until all the solids are essentially under 50 microns, reblended, and packaged.

EXAMPLE 2

Wettable Power

3-[1-(1,2-difluoro-2-chloroethenyl)]-N-[4-methoxy-6-methylpyrimidin-2-yl)aminocarbonyl]-2-pyridine-sulfonamide 50% sodium alkylnaphthalenesulfonate 2%
low viscosity methyl cellulose 2%
diatomaceous earth 46%

The ingredients are blended, coarsely hammer-milled and then air-milled to produce particles essentially all below 10 microns in diameter. The product is reblended before packaging.

EXAMPLE 3

Granule

Wettable Powder of Example 2 5%
attapulgite granules 95%
(U.S.S. 20–40 mesh; 0.84–0.42 mm)

A slurry of wettable powder containing 25% solids is sprayed on the surface of attapulgite granules in a double-cone blender. The granules are dried and packaged.

EXAMPLE 4

Extruded Pellet

3-[1-(1,2-difluoro-2-chloroethenyl)]-N-[4-methoxy-6-methylpyrimidin-2-yl)aminocarbonyl]-2-pyridine-sulfonamide 25% anhydrous sodium sulfate 10%
crude calcium ligninsulfonate 5%
sodium alkylnaphthalenesulfonate 1%
calcium/magnesium bentonite 59%

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 5

Oil Suspension

3-[1-(1,2-difluoro-2-chloroethenyl)]-N-[4-methoxy-6-methylpyrimidin-2-yl)aminocarbonyl]-2-pyridine-sulfonamide 25% polyoxyethylene sorbitol hexaoleate 5%
highly aliphatic hydrocarbon oil 70%

The ingredients are ground together in a sand mill until the solid particles have been reduced to under about 5 microns. The resulting thick suspension may be applied directly, but preferably after being extended with oils or emulsified in water.

EXAMPLE 6

Wettable Powder

3-[1-(1,2-difluoro-2-chloroethenyl)]-N-[4-methoxy-6-methylpyrimidin-2-yl)aminocarbonyl]-2-pyridine-sulfonamide 20% sodium alkylnaphthalenesulfonate 4%
sodium ligninsulfonate 4%
low viscosity methyl cellulose 3%
attapulgite 69%

The ingredients are thoroughly blended. After grinding in a hammer-mill to produce particles essentially all below 100 microns, the material is reblended and sifted through a U.S.S. No. 50 sieve (0.3 mm opening) and packaged.

EXAMPLE 7

Low Strength Granule

3-[1-(1,2-difluoro-2-chloroethenyl)]-N-[4-methoxy-6-methylpyrimidin-2-yl)aminocarbonyl]-2-pyridine-sulfonamide 1%

N,N-dimethylformamide 9%
attapulgite granules 90%
(U.S.S. 20-40 sieve)

The active ingredient is dissolved in the solvent and the solution is sprayed upon dedusted granules in a double cone blender. After spraying of the solution has been completed, the blender is allowed to run for a short period and then the granules are packaged.

EXAMPLE 8

Aqueous Suspension

3-[1-(1,2-difluoro-2-chloroethenyl)]-N-[4-methoxy-6-methylpyrimidin-2-yl)aminocarbonyl]-2-pyridine-sulfonamide 40% polyacrylic acid thickener 0.3%
dodecylphenol polyethylene glycol ether 0.5%
disodium phosphate 1%
monosodium phosphate 0.5%
polyvinyl alcohol 1.0%
water 56.7%

The ingredients are blended and ground together in a sand mill to produce particles essentially all under 5 microns in size.

EXAMPLE 9

Solution

3-[1-(1,2-difluoro-2-chloroethenyl)]-N-[4-methoxy-6-methylpyrimidin-2-yl)aminocarbonyl]-2-pyridine-sulfonamide. 5% water 95%

The salt is added directly to the water with stirring to produce the solution, which may then be packaged for use.

EXAMPLE 10

Low Strength Granule

3-[1-(1,2-difluoro-2-chloroethenyl)]-N-[4-methoxy-6-methylpyrimidin-2-yl)aminocarbonyl]-2-pyridine-sulfonamide 0.1% attapulgite granules 99.9%
(U.S.S. 20-40 mesh)

The active ingredient is dissolved in a solvent and the solution is sprayed upon dedusted granules in a double-cone blender. After spraying of the solution has been completed, the material is warmed to evaporate the solvent. The material is allowed to cool and then packaged.

EXAMPLE 11

Granule

3-[1-(1,2-difluoro-2-chloroethenyl)]-N-[4-methoxy-6-methylpyrimidin-2-yl)aminocarbonyl]-2-pyridine-sulfonamide 80% wetting agent 1%
crude ligninsulfonate salt (containing 5-20% of the natural sugars) 10%
attapulgite clay 9%

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14-100 mesh (1410-149 microns), and packaged for use.

EXAMPLE 12

High Strength Concentrate

3-[1-(1,2-difluoro-2-chloroethenyl)]-N-[4-methoxy-6-methylpyrimidin-2-yl)aminocarbonyl]-2-pyridine-sulfonamide 99% silica aerogel 0.5%
synthetic amorphous silica 0.5%

The ingredients are blended and ground in a hammer-mill to produce a material essentially all passing to U.S.S. No. 50 screen (0.3 mm opening). The concentrate may be formulated further if necessary.

EXAMPLE 13

Wettable Powder

3-[1-(1,2-difluoro-2-chloroethenyl)]-N-[4-methoxy-6-methylpyrimidin-2-yl)aminocarbonyl]-2-pyridine-sulfonamide 90% dioctyl sodium sulfosuccinate 0.1%
synthetic fine silica 9.9%

The ingredients are blended and ground in a hammer-mill to produce particles essentially all below 100 microns. The material is sifted through a U.S.S. No. 50 screen and then packaged.

EXAMPLE 14

Wettable Powder

3-[1-(1,2-difluoro-2-chloroethenyl)]-N-[4-methoxy-6-methylpyrimidin-2-yl)aminocarbonyl]-2-pyridine-sulfonamide 40% sodium ligninsulfonate 20%
montmorillonite clay 40%

The ingredients are throughly blended, coarsely hammer-milled and then air-milled to produce particles essentially all below 10 microns in size. The material is reblended and then packaged.

EXAMPLE 15

Oil Suspension

3-[1-(1,2-difluoro-2-chloroethenyl)]-N-[4-methoxy-6-methylpyrimidin-2-yl)aminocarbonyl]-2-pyridine-sulfonamide 35% blend of polyalcohol carboxylic esters of oil soluble petroleum sulfonates 6%
xylene 59%

The ingredients are combined and ground together in a sand mill to produce particles essentially all below 5 microns. The product can be used directly, extended with oils, or emulsified in water.

EXAMPLE 16

Dust

3-[1-(1,2-difluoro-2-chloroethenyl)]-N-[4-methoxy-6-methylpyrimidin-2-yl)aminocarbonyl]-2-pyridine-sulfonamide 10% attapulgite 10%
Pyrophyllite 80%

The active ingredient is blended with attapulgite and then passed through a hammer-mill to produce particles substantially all below 200 microns. The ground concentrate is then blended with powdered pyrophyllite until homogeneous.

EXAMPLE 17

Emulsifiable Concentrate

3-[1-(1,2-difluoro-2-chloroethenyl)]-N-[4-methoxy-6-methylpyrimidin-2-yl)aminocarbonyl]-2-pyridine-sulfonamide 10% chlorobenzene 84%
sorbitan monostearate and polyoxyethylene condensates thereof 6%

The ingredients are combined and stirred to produce a solution which can be emulsified in water for application.

Utility

Test results indicate that the compounds of the present invention are highly active preemergent or postemergent herbicides or plant growth regulators. Many of them have utility for broad-spectrum pre- and or post-emergence weed control in areas where complete control of all vegetation is desired, such as around fuel storage tanks, ammunition depots, industrial storage areas, parking lots, drive-in theaters, around billboards, highway and railroad structures. Some of the compounds have utility for selective weed control in crops such as rice and wheat. Alternatively, the subject compounds are useful to modify plant growth.

The rates of application for the compounds of the invention are determined by a number of factors, including their use as plant growth modifiers or as herbicides, the crop species involved, the types of weeds to be controlled, weather and climate, formulations selected, mode of application, amount of foliage present, etc. In general terms, the subject compounds should be applied at levels of around 0.05 to 10 kg/ha, the lower rates being suggested for use on lighter soils and/or those having a low organic matter content, for plant growth modification or for situations where only short-term persistence is required.

The compounds of the invention may be used in combination with any other commercial herbicide, examples of which are those of the triazine, triazole, uracil, urea, amide, diphenylether, carbamate and bipyridylium types.

What is claimed is:

1. A compound of the formula $$\text{LSO}_2\text{NHC}\overset{W_3}{\overset{\|}{\text{C}}}\text{NA} \underset{R}{|} \qquad I$$

wherein

L is $R_1$—[pyridine ring with $(\phantom{})_n$—W substituent]— (L-1) or $R_1$—[pyridine ring with —$(\phantom{})_n$W substituent]— (L-2);

R is H or $CH_3$;
$W_3$ is O or S;
n is 0 or 1;
$R_1$ is H, $C_1$–$C_3$ alkyl, $C_1$–$C_3$ haloalkyl, halogen, nitro, $CH_2CN$, $CH_2OCH_3$, $CH_2SCH_3$, CN, $C_1$–$C_3$ alkoxy, $SO_2NR^I R^{II}$, $C_1$–$C_3$ alkylthio, $C_1$–$C_3$ alkylsulfinyl, $C_1$–$C_3$ alkylsulfonyl or $CO_2R^{III}$;
$R^I$ is H, $C_1$–$C_4$ alkyl, $C_2$–$C_3$ cyanoalkyl, methoxy or ethoxy;
$R^{II}$ is H, $C_1$–$C_4$ alkyl or $C_3$–$C_4$ alkenyl; or
$R^I$ and $R^{II}$ may be taken together as —$(CH_2)_3$—, —$(CH_2)_4$—, —$(CH_2)_5$— or —$CH_2CH_2OCH_2CH_2$—;
$R^{III}$ is $C_1$–$C_4$ alkyl, $C_3$–$C_4$ alkenyl, $C_3$–$C_4$ alkynyl, $C_2$–$C_4$ haloalkyl, $C_2$–$C_4$ cyanoalkyl, $C_5$–$C_6$ cycloalkyl, $C_4$–$C_7$ cycloalkylalkyl or $C_2$–$C_4$ alkoxyalkyl;
W is $W_1$;
$W_1$ is $C_2$–$C_8$ alkenyl substituted with 1–3 atoms of F, Cl or Br;

A is —$CH_2$—[pyrimidine ring with $OCH_3$ and $X_3$ substituents]  A-6

$X_3$ is $CH_3$ or $OCH_3$;
and their agriculturally suitable salts.

2. The compounds of claim 1 where
R is H; and
$W_3$ is O.

3. The compounds of claim 2 where
R$_1$ is H, F, Cl, NO$_2$, C$_1$-C$_2$ alkyl, C$_1$-C$_2$ haloalky, C$_1$-C$_2$ alkoxy, C$_1$-C$_2$ alkylthio, CH$_2$OCH$_3$ or CH$_2$SCH$_3$, and is not para to the sulfonylurea bridge.

4. The compounds of claim 3 where W$_1$ is C$_2$-C$_5$ alkenyl substituted by 1-3 atoms of F, Cl or Br.

5. The compounds of claim 4 where
R$_1$ is H, CH$_3$, OCH$_3$ or Cl.

6. The compounds of claim 4 where L is L-1.

7. The compounds of claim 4 where L is L-2.

8. An agriculturally suitable composition for controlling the growth of undesired vegetation comprising an effective amount of a compound of claim 1 and at least one of the following: surfactant, solid or liquid diluent.

9. An agriculturally suitable composition for controlling the growth of undesired vegetation comprising an effective amount of a compound of claim 2 and at least one of the following: surfactant, solid or liquid diluent.

10. An agriculturally suitable composition for controlling the growth of undesired vegetation comprising an effective amount of a compound of claim 3 and at least one of the following: surfactant, solid or liquid diluent.

11. An agriculturally suitable composition for controlling the growth of undesired vegetation comprising an effective amount of a compound of claim 5 and at least one of the following: surfactant, solid or liquid diluent.

12. An agriculturally suitable composition for controlling the growth of undesired vegetation comprising an effective amount of a compound of claim 5 and at least one of the following: surfactant, solid or liquid diluent.

13. An agriculturally suitable composition for controlling the growth of undesired vegetation comprising an effective amount of a compound of claim 6 and at least one of the following: surfactant, solid or liquid diluent.

14. An agriculturally suitable composition for controlling the growth of undesired vegetation comprising an effective amount of a compound of claim 7 and at least one of the following: surfactant, solid or liquid diluent.

15. A method for controlling the growth of undesired vegetation which comprises applying to the locus to be protected an effective amount of a compound of claim 1.

16. A method for controlling the growth of undesired vegetation which comprises applying to the locus to be protected an effective amount of a compound of claim 2.

17. A method for controlling the growth of undesired vegetation which comprises applying to the locus to be protected an effective amount of a compound of claim 3.

18. A method for controlling the growth of undesired vegetation which comprises applying to the locus to be protected an effective amount of a compound of claim 4.

19. A method for controlling the growth of undesired vegetation which comprises applying to the locus to be protected an effective amount of a compound of claim 5.

20. A method for controlling the growth of undesired vegetation which comprises applying to the locus to be protected an effective amount of a compound of claim 6.

21. A method for controlling the growth of undesired vegetation which comprises applying to the locus to be protected an effective amount of a compound of claim 7.

* * * * *